(12) United States Patent
Schubert

(10) Patent No.: US 7,285,782 B2
(45) Date of Patent: Oct. 23, 2007

(54) INFRARED SENSOR WITH EXPLOSION-PROOF PROTECTION FOR GAS METERING APPLIANCES

(75) Inventor: Axel Schubert, Berlin (DE)

(73) Assignee: MSA Auer GmbH, Berlin (DE)

( * ) Notice: Subject to any disclaimer, the term of this patent is extended or adjusted under 35 U.S.C. 154(b) by 294 days.

(21) Appl. No.: 10/514,144

(22) PCT Filed: Mar. 27, 2003

(86) PCT No.: PCT/DE03/01047

§ 371 (c)(1),
(2), (4) Date: Nov. 8, 2004

(87) PCT Pub. No.: WO03/095990

PCT Pub. Date: Nov. 20, 2003

(65) Prior Publication Data

US 2005/0230624 A1    Oct. 20, 2005

(30) Foreign Application Priority Data

May 14, 2002   (DE) ................ 102 21 954

(51) Int. Cl.
*G01J 5/02* (2006.01)
(52) U.S. Cl. ................. 250/339.13
(58) Field of Classification Search ........... 250/339.13, 250/343
See application file for complete search history.

(56) References Cited

U.S. PATENT DOCUMENTS

| | | | |
|---|---|---|---|
| 3,560,738 A * | 2/1971 | Strange ............. | 250/343 |
| 3,788,751 A | 1/1974 | Shimazaki et al. | |
| 3,860,818 A | 1/1975 | Stalder et al. | |
| 4,177,381 A | 12/1979 | McClatchie et al. | |
| 4,709,150 A * | 11/1987 | Burough et al. ......... | 250/338.1 |
| 4,818,875 A | 4/1989 | Weiner | |
| 5,222,389 A * | 6/1993 | Wong ................ | 73/31.02 |
| 5,281,816 A | 1/1994 | Jacobson et al. | |
| 5,753,797 A * | 5/1998 | Forster et al. ............ | 73/24.01 |
| 6,155,160 A * | 12/2000 | Hochbrueckner ........... | 99/331 |
| 6,469,303 B1 * | 10/2002 | Sun et al. .................. | 250/343 |

FOREIGN PATENT DOCUMENTS

| | | |
|---|---|---|
| DE | 1 773 602 | 11/1971 |
| DE | 2 303 037 | 7/1974 |
| DE | 198 08 128 | 8/1998 |
| DE | 199 00 129 | 8/2000 |
| DE | 199 51 163 | 5/2001 |
| DE | 100 63 024 | 8/2001 |
| GB | 2317010 A * | 3/1998 |
| JP | 2002-22655 | 1/2002 |
| WO | WO94/18546 | 8/1994 |

* cited by examiner

*Primary Examiner*—David Porta
*Assistant Examiner*—Djura Malevic
(74) *Attorney, Agent, or Firm*—Wood, Phillips, Katz, Clark & Mortimer

(57) ABSTRACT

An infrared sensor for gas metering appliances consisting of a metering chamber with an infrared source and an infrared sensor. The metering chamber is connected to the atmosphere via an anti-dust and anti-damp filter. The metering chamber is arranged in a protective housing having gas inlets and outlets. Connection to the metering chamber via a gas exchanger orifice and an anti-dust and anti-damp filter is not of a pressure-proof design based on normal pressure conditions. The infrared source and the infrared detector are integrated in the wall of the metering chamber and held therein. The infrared source is a lamp. The infrared source and infrared detector have a fail-safe power supply.

7 Claims, 3 Drawing Sheets

INFRARED SENSOR WITH EXPLOSION-PROOF PROTECTION FOR GAS METERING APPLIANCES

This invention relates to an infrared sensor for gas-measuring devices with approved explosion protection consisting of a housing in which an infrared source and an infrared detector are placed in a measuring chamber that communicates with the gas atmosphere through a dust and moisture filter.

Measuring devices for detecting gas hazards caused by explosive or harmful gases, or by oxygen deficiency or excess oxygen, are used in many industrial branches such as in mining and the chemical industry as well as for environmental protection and disaster control operations. These devices are equipped with infrared sensors for detecting and measuring harmful gases, each comprising an infrared sensor and detector in the interior of a housing into which gas flows via a filter. The infrared detector detects the thermal spectra produced when infrared rays generated by the infrared source pass the respective gas as a measure of gas composition.

To ensure that the infrared sensors meet maximum safety and explosion protection requirements, infrared source and infrared detector are housed in a pressure-proof housing that forms a "d" type of protection enclosure. Under the current explosion protection regulations, infrared sensors that meet the requirements of this type of protection are not suitable for use in areas rated zone 0 that are exposed to permanent, frequent, or long-term gas hazards, however rare such use may be as 95% of the gas-measuring devices with infrared sensors are used in areas rated zone 1 where there is only an occasional harmful gas hazard. The gas enters the housing through an intrinsically pressure-proof sintered material that is fitted into the shell of the housing in a pressure-proof manner and acts as a filter. When the lamp preferred for cost reasons as infrared source breaks and the gases ignite on the hot coil of the lamp, the pressure-proof enclosure prevents an explosion as the gases ignited inside the housing cannot get outside and any ignition outside is prevented. These infrared sensors, however, require expensive high-precision manufacturing due to the pressure-proof design of the housing and the gas inlet and outlet and will only allow a slow gas exchange through the pressure-proof filter material, due to the high resistance.

This disadvantage is eliminated in a known infrared sensor in that the infrared source alone is in a pressure-proof enclosure while the infrared rays reach the infrared detector through a sapphire window. While this design allows free gas exchange, the optical path of the rays and thus their infrared range is attenuated by the sapphire window, leading to signal loss that influences the result of measurement. In addition, achieving a pressure resistance of 10 bar or more requires extensive testing.

It is therefore the problem of this invention to provide a reasonably priced infrared sensor for gas measuring devices to be used in hazard zone 1 that can be made without a major manufacturing and testing effort, ensures fast gas exchange and accurate results of measurement, an improved embodiment of which being suitable for hazard zone 0 with exposure to permanent or frequent gas hazards.

This problem is solved according to the invention by the infrared sensor comprising the characteristics described in claim 1.

The inventive idea is that a protective housing that is impact-proof up to a certain collision energy and onto or into which a likewise impact-proof and highly permeable dust and moisture filter is fitted, encloses the infrared sensor, i.e. the measuring chamber or section that contains the infrared source and infrared detector. The impact-proof protective housing prevents both the destruction of the infrared source and the associated risk of ignition and damage to the dust and moisture filter that also reduces the risk of igniting the gases. This sensor that can be made with little manufacturing and testing effort ("e" type of protection for increased safety) can be used in hazard zone 1 that accounts for 95% of all cases in which measurements are made. The gas flows through the measuring chamber without any considerable delay.

According to another characteristic of the invention that can alternatively be added to the characteristics listed above, said impact-proof protective housing including the dust and moisture filter attached to its gas inlet and outlet have a pressure-proof design up to a specific interior pressure. The infrared sensor improved in this way combines two types of protection, i. e. "e" type of protection (impact-proof, increased safety) and "d" type of protection (pressure-proof) and may therefore also be used in hazard zone 0 (permanent, long-term, or frequent gas hazard), if the resulting delay of the gas flow to the measuring chamber due to the pressure-proof design of the dust and moisture filter and added production cost for the pressure-proof design are acceptable.

According to another characteristic of the invention, the infrared source, which can be a reasonably priced lamp due to the impact-proof design of the protective housing, and the infrared detector as well as their respective power supplies or electronics are intrinsically safe, which further reduces the risk of igniting explosive gases.

In one aspect of the invention, the interior of the impact-proof protective housing at the same time forms the measuring chamber, and the dust and moisture filters are directly fitted into or onto the gas inlet and outlet openings.

In another aspect of the invention, the measuring chamber is a separate casing with a gas exchange opening that is located inside the protective housing and contains the infrared source and the infrared detector. This gas exchange opening is covered with a highly permeable dust and moisture filter in the non-pressure-proof design of the protective housing whereas the pressure-proof protective housing is already equipped with a pressure-proof dust and moisture filter so that the gas exchange opening does not have to be covered.

If gas is measured by pump operation, gas is supplied and discharged via fittings that are attached to the protective housing and to which gas lines can be connected. To protect these fittings from destruction by impact, another aspect of the invention includes an impact-protection block for the gas inlet and outlet openings in the protective housing. This impact-protection block includes two gas ducts that are connected to the gas inlet or outlet and run horizontally towards the shell of the protective housing, to the outer ends of which the respective fitting is connected which will then be protected against impacts. A dust and moisture filter supported by the impact-protection block is fitted into or onto the gas inlet and outlet openings and is either highly permeable or pressure-proof depending on the intended use of the infrared sensor in a hazard zone 1 or 0.

Pressure, humidity, and temperature sensors are provided in the measuring chamber either in a separate interior casing or directly in the interior of the protective housing to compensate pressure, humidity, and temperature differences when measuring gas.

Other useful aspects of this invention can be derived from the embodiments described below and from the claims.

Embodiments of the invention are explained in greater detail with reference to the figures. Wherein.

Figure 4:
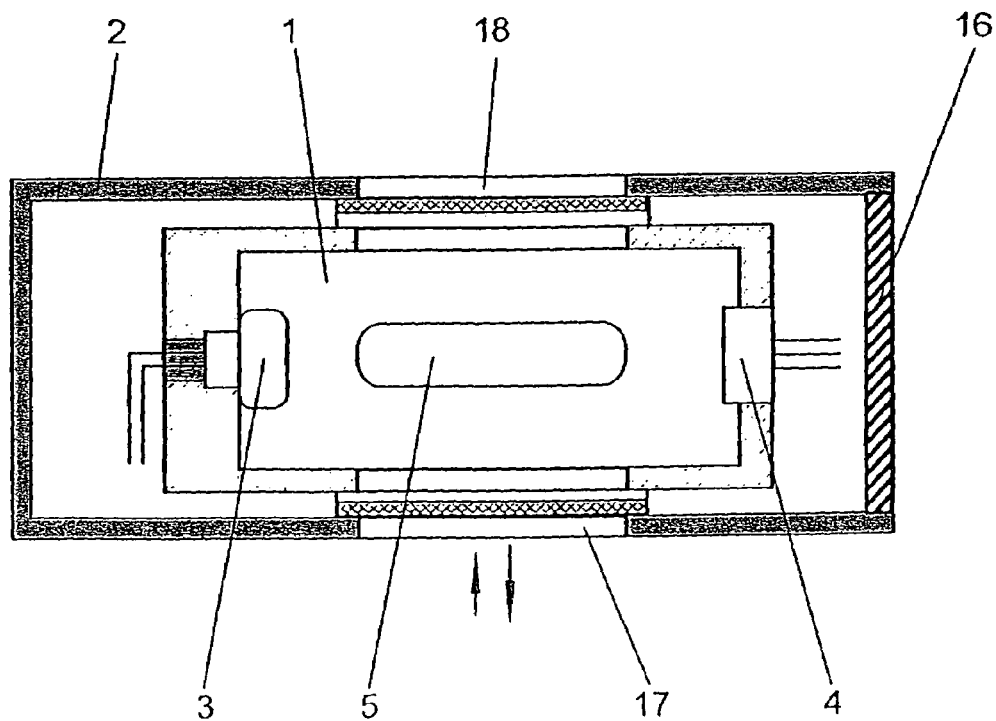
Figure 5:
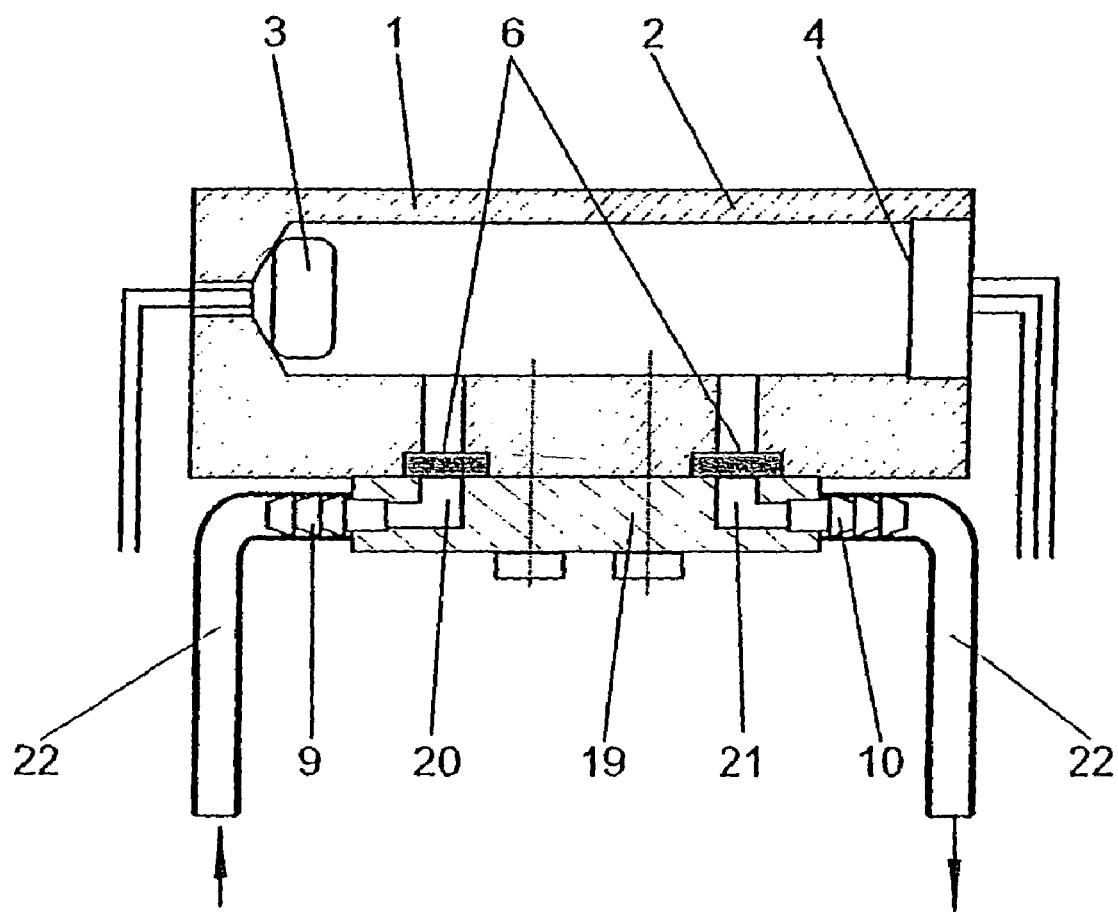

FIG. 4 shows another embodiment of an infrared sensor that may also be used in hazard zone 0; and FIG. 5 shows yet another embodiment of an impact-proof design of an infrared sensor for gas measurement in hazards zone 1, or, with pressure-proof installation, in hazard zone 0.

Figure 1:
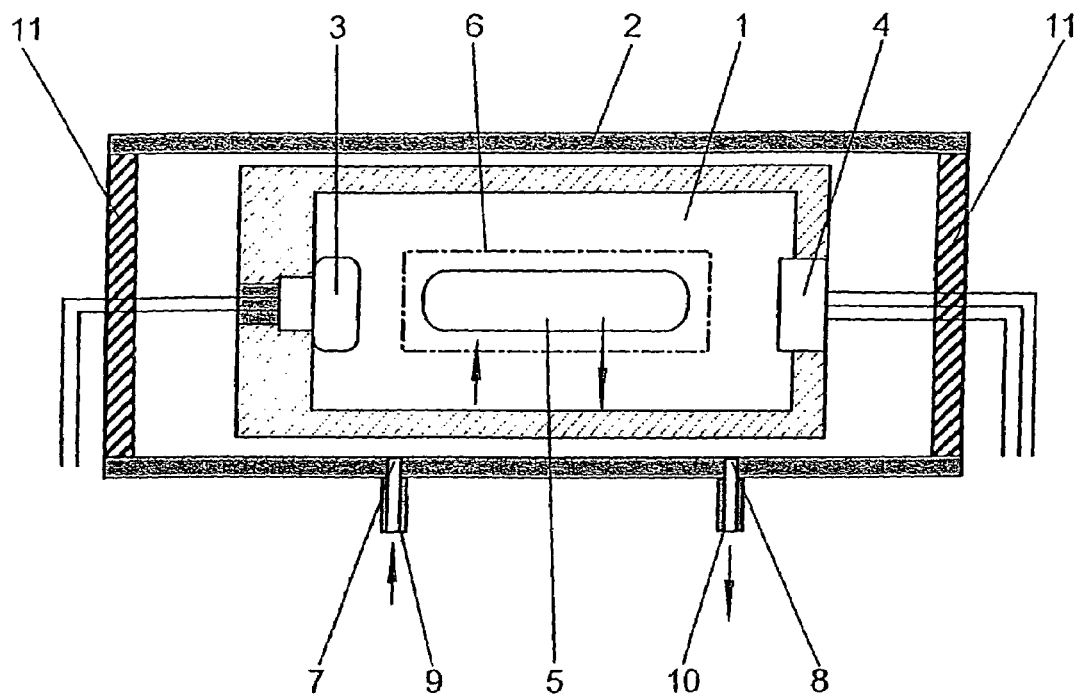
FIG. 1 shows a sectional view of an impact-proof design of the infrared sensor according to the invention with "e" type of protection for gas measurement in zone 1 areas with an occasional gas hazard.

The infrared sensor according to FIG. 1 comprises a measuring chamber 1 surrounded at a spacing by a protective housing 2 that is impact-proof up to an impact load of at least seven joule. While measuring chamber 1, for example, consists of easily ductile aluminum, the protective housing 2 is made of a super high strength material such as super high strength aluminum with a specific wall thickness or stainless steel. The measuring chamber 1 and the protective housing 2 are not pressure-proof according to "d" type of protection. A lamp serving as infrared source 3 is glued to one end panel of the cylindrical measuring chamber 1, and an infrared detector 4 is glued to the other end panel. While a reasonably priced lamp is used as infrared source 3, the infrared detector is a semiconductor detector such as a pyrosensor, photo diode, or thermocouple pile. The semiconductor detector has an intrinsically safe design due to its low rating. The lamp 3 is supplied via an intrinsically safe power supply so that this does not cause any risk of ignition. An oblong gas exchange opening 5 is located in the cylinder wall of the measuring chamber 1 (measuring cylinder, separate inner casing) and closed by a dust and moisture filter 6 with an IP44 protective system. The dust and moisture protection for measuring chamber 1 may either be wire gauze or a highly permeable plastic body or a sintered material. The dust and moisture filter 6 that reduces the ignitibility of the respective gases is also protected against impacts and destruction by the protective housing 2. The cylinder wall of the protective housing 2 comprises a gas inlet opening 7 and, at a distance from this, a gas outlet opening 8 connected to a pump (not shown) via the fittings 9, 10. The gas to be measured by this infrared sensor working in pump-operated mode is a gas stream that flows without delay via the gas inlet opening 7 and the gas exchange opening 5 with the dust and moisture filter 6 into the measuring section formed by the lamp 3 and the infrared detector 4 and is discharged through the gas outlet opening 8.

The infrared source 3 and the infrared detector 4 can, for example, be glued in such a way into the opposite end panels of the measuring casing that these are securely mounted. Destruction of the glass bulb of the lamp and exposure of its heating coil as a source of ignition cannot even be effected by extreme impacts hitting on the infrared sensor as the components on the inside of the protective housing 2 and the end panels 11 in the protective housing 2 cannot be damaged due to its impact-proof design.

Due to the impact-proof and dust-proof design of the infrared sensor with the "e" type of protection, this sensor can be operated like an infrared sensor in a pressure-proof enclosure with the "d" type of protection in hazard zone 1 environments, which includes about 95% of all applications. However, the manufacturing and testing effort for an infrared sensor with the "e" type of protection is considerably less than for an infrared sensor with a pressure-proof enclosure according to the "d" type of protection used under the same conditions.

Figure 2:
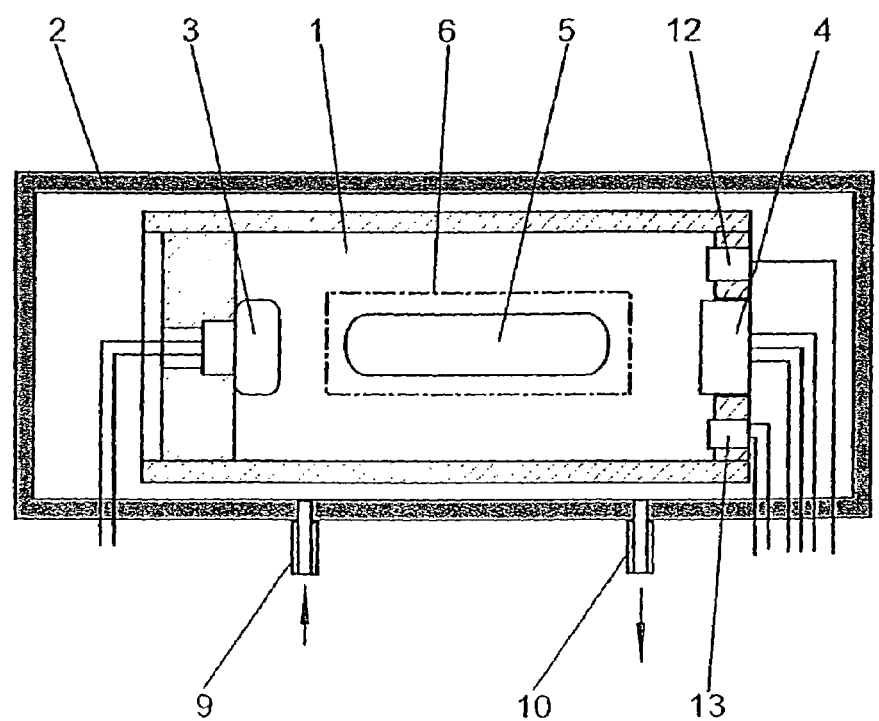
FIG. 2 shows a modified design of the infrared sensor shown in FIG. 1 that has disturbance variable compensation.

An extended embodiment of the infrared sensor shown in FIG. 1 is shown in FIG. 2. This infrared sensor in which the infrared detector 4 comprises at least one gas-specific gas measuring channel $\lambda 1, \lambda 2, \lambda 3$ and a reference channel $\lambda 0$ for a 0 signal further includes a temperature and humidity sensor 12 and a pressure sensor 13 on the infrared detector 4. In this way, temperatures, moisture and pressures that influence the result of measurement can be taken into account or compensated.

Figure 3:
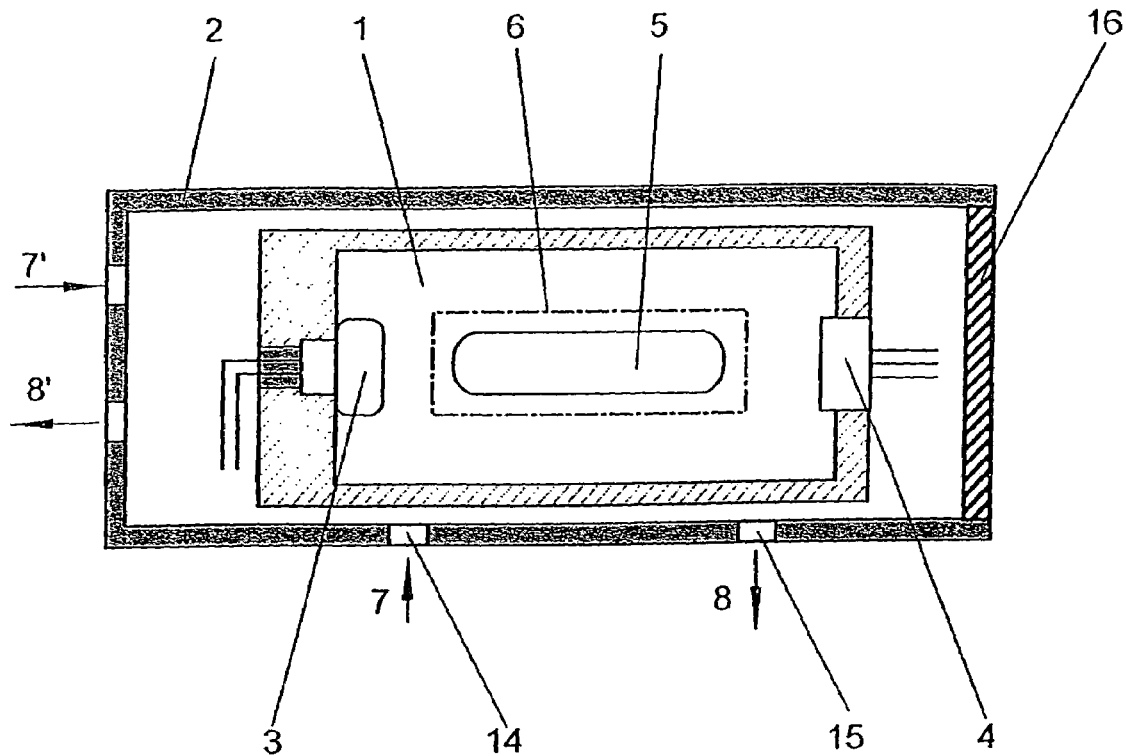
FIG. 3 shows an extended embodiment of the infrared sensor shown in FIG. 1 that combines two types of protection, i. e. an impact-proof design ("e" type of protection) and a pressure-proof enclosure ("d" type of protection) for use in hazard zone 0 with a long-term or frequently occurring gas hazard.

FIG. 3 shows an infrared sensor approved for use in hazard zone 0 that can also be pump-operated. In this case, the measuring chamber 1 is designed as shown in the embodiments represented in FIGS. 1 and 2, and the protective housing is impact-proof. In addition, measuring chamber 1 has a pressure-proof enclosure in that the protective housing 2 is pressure-proof. For this purpose, the gas inlet opening 7 and the gas outlet opening 8 have the dust and moisture filter 15, 14 made of sintered material as a pressure-proof covering, and even the mounting hole caps 16 of the protective housing 2 are fitted and glued or cast in to provide pressure resistance. Thus an infrared sensor is provided that combines the two independent "e" (increased safety) and "d" (pressure-proof enclosure) types of protection. This infrared sensor meets highest safety requirements by providing two separate types of protection and may be used in hazard zone 0. FIG. 3 also shows two different gas inlet/outlet configurations 7, 8 or 7', 8'.

The embodiment represented in FIG. 4 is a variant of an impact-proof ("e" type of protection) and a pressure-proof ("d" type of protection) design of an infrared sensor operating on the diffusion principle in hazard zone 0. Unlike the embodiment shown in FIG. 3, the perimeter of the protective housing 2 shows large dust and moisture filters 17, 18 made of pressure-proof sintered material that provides IP54 dust-proof protection. The gas exchange openings 5 in the measuring chamber 1 are placed at an offset from the filters made of sintered material (dust and moisture filters 17, 18).

FIG. 5 shows an infrared sensor designed for pump operation whose measuring chamber 1 is directly formed by the interior of the protective housing 2. The infrared detector 4 and the infrared source 3 that have an intrinsically safe supply according to "i" type of protection are located at the end panels of the protective housing. The gas inlet and outlet openings 7, 8 provided in the protective housing 2 are covered with a highly permeable dust and moisture filter 6 (IP44 dust-proof protective system). A gas manifold for fittings 9, 10 underneath the gas inlet and outlet openings 7, 8 is used as an impact-protection block 19. The interior of said impact-protection block 19 comprises two gas ducts 20, 21 that connect the gas inlet opening 7 to the fitting 9 and the gas outlet opening 8 to the fitting 10. The fittings 9, 10 at the front panel of the impact-protection block 19 run in horizontal direction from the protective housing 2 and are therefore protected against impact. The dust and moisture filters 6 are also protected by said impact-protection block 19. Gas lines 22 from a pump (not shown) are connected to the fitting.

The infrared sensor described last that has an impact-proof and intrinsically safe design ("e" and "i" types of protection) can additionally meet the requirements of the "d" type of protection by integrating the infrared source 3 and the infrared detector 4 into the pressure-proof protective housing 2 and by using dust and moisture filters 14, 15 with the IP54 dust-proof protective system. In this case, the infrared sensor may be used in hazard zone 0 with permanent or frequent risk of explosion.

LIST OF REFERENCE SYMBOLS

1 Measuring chamber (separate casing)
2 Impact-proof protective housing
3 Infrared source (lamp)
4 Infrared detector (semiconductor detector)
5 Gas exchange opening in 1
6 Highly permeable dust and moisture filter
7 Gas inlet opening
8 Gas outlet opening
9 Fitting
10 Fitting
11 End panels
12 Temperature and humidity sensor
13 Pressure sensor
14 Pressure-proof dust and moisture filter (pump operation)
15 Pressure-proof dust and moisture filter (pump operation)
16 Mounting hole cap
17 Pressure-proof dust and moisture filter (diffusion operation)
18 Pressure-proof dust and moisture filter (diffusion operation)
19 Impact protection block
20 Gas duct in 19
21 Gas duct in 19
22 Gas line

The invention claimed is:

1. An infrared sensor for gas metering appliances comprising:
a metering casing having a metering chamber wherein an infrared lamp and an infrared sensor are integrated, wherein:
a) the metering casing is made of a ductile material and is arranged in a protective housing made of a high strength material which has an impact resistance to loads of at least seven joule;
b) the metering casing comprises at least a gas inlet and gas outlet opening with an anti-dust and anti-damp filter which comprises a wire gauze or a highly permeable plastic material;
c) the protective housing comprises gas inlet and gas outlet openings; and
d) the infrared lamp and infrared detector each has a fail-safe power supply.

2. The infrared sensor according to claim 1, wherein fittings for gas supply and discharge in pump operation are provided on the outside of the protective housing.

3. The infrared sensor according to claim 1, wherein said gas inlet and gas outlet openings in the separate metering casing are placed at an offset from the gas inlet and outlet openings in the protective housing or from the anti-dust and anti-damp filters that cover the gas inlet and gas outlet openings in the metering casing.

4. The infrared sensor according to claim 1, wherein the protective housing has gas inlet and gas outlet openings with anti-dust and anti-damp filters.

5. The infrared sensor according to claim 4, characterized in that the anti-dust and anti-damp filters comprise a sintered material.

6. The infrared sensor according to claim 1, wherein the metering chamber is directly formed by the interior of the protective housing, and the infrared lamp and the infrared detector as well as the anti-dust and anti-damp filters are provided in/on the wall of said protective housing.

7. The infrared sensor according to claim 1, wherein a block is provided with gas ducts that at one end are connected to a respective gas inlet or gas outlet opening in the protective housing and at the other end are connected to a respective fitting that runs in horizontal direction from the protective housing, and said anti-dust and anti-damp filters are placed either in or on said gas inlet and outlet gas openings in the protective housing.

* * * * *